US010350393B2

(12) United States Patent
Graves et al.

(10) Patent No.: US 10,350,393 B2
(45) Date of Patent: *Jul. 16, 2019

(54) CHECKER BALLOON WINDING MACHINE

(71) Applicant: C.R. BARD, INC., Murray Hill, NJ (US)

(72) Inventors: David M. Graves, Mesa, AZ (US); William E. Parmentier, Gilbert, AZ (US); Robert G. Lerdahl, Phoenix, AZ (US); Phillip E. Carr, Fountain Hills, AZ (US); Jo Ann Kelly, Tempe, AZ (US)

(73) Assignee: C.R. BARD, INC., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/495,462

(22) Filed: Apr. 24, 2017

(65) Prior Publication Data

US 2017/0224966 A1 Aug. 10, 2017

Related U.S. Application Data

(60) Continuation of application No. 14/188,066, filed on Feb. 24, 2014, now Pat. No. 9,643,235, which is a (Continued)

(51) Int. Cl.
*A61M 25/10* (2013.01)
*B65H 54/28* (2006.01)
(Continued)

(52) U.S. Cl.
CPC ......... *A61M 25/1029* (2013.01); *A61F 2/958* (2013.01); *A61M 25/1027* (2013.01);
(Continued)

(58) Field of Classification Search
CPC ...... A61M 25/1029; A61M 2025/1086; A61M 2025/1031; B65H 57/02; B65H 71/00; B65H 54/28; B65H 57/14
See application file for complete search history.

(56) References Cited

U.S. PATENT DOCUMENTS

| | | | |
|---|---|---|---|
| 6,616,651 B1 * | 9/2003 | Stevens | A61M 25/0012 604/103.09 |
| 2002/0030134 A1 * | 3/2002 | Sugiuchi | H01F 41/076 242/445.1 |

(Continued)

*Primary Examiner* — Robert J Grun
(74) *Attorney, Agent, or Firm* — King & Schickli, PLLC

(57) ABSTRACT

A device for winding a filament around a structure disposed concentrically around a distal end of a balloon catheter includes a rotatable holder for retaining a distal end of the balloon catheter, a translatable winding carriage for helically winding the tensioned filament around the balloon catheter distal end, a heater for applying a predetermined amount of heat to a section of the balloon catheter having the filament wound therearound, and a controller for controlling at least the rate of rotation of the holder, the tensioning force applied to the filament, the amount of heat applied by the heater, and the rate of travel of the translatable winding carriage along the longitudinal dimension of the balloon catheter. By use of the device, the balloon is heat set and a predetermined checkering pattern of surface indentations are provided in the structure exterior surface in a single pass.

17 Claims, 11 Drawing Sheets

Related U.S. Application Data continuation of application No. 13/563,126, filed on Jul. 31, 2012, now Pat. No. 8,673,200, which is a division of application No. 12/497,166, filed on Jul. 2, 2009, now Pat. No. 8,236,223.

(51) Int. Cl.
  *B65H 57/02* (2006.01)
  *B65H 57/14* (2006.01)
  *B65H 71/00* (2006.01)
  *A61F 2/958* (2013.01)
  *B21F 3/02* (2006.01)

(52) U.S. Cl.
  CPC .............. *B21F 3/02* (2013.01); *B65H 54/28* (2013.01); *B65H 57/02* (2013.01); *B65H 57/14* (2013.01); *B65H 71/00* (2013.01); *A61M 2025/1031* (2013.01); *A61M 2025/1086* (2013.01)

(56) References Cited

U.S. PATENT DOCUMENTS

| | | | |
|---|---|---|---|
| 2003/0014100 A1* | 1/2003 | Maria Meens | A61F 2/958 623/1.11 |
| 2009/0159736 A1* | 6/2009 | Asano | H01F 41/096 242/444 |

* cited by examiner

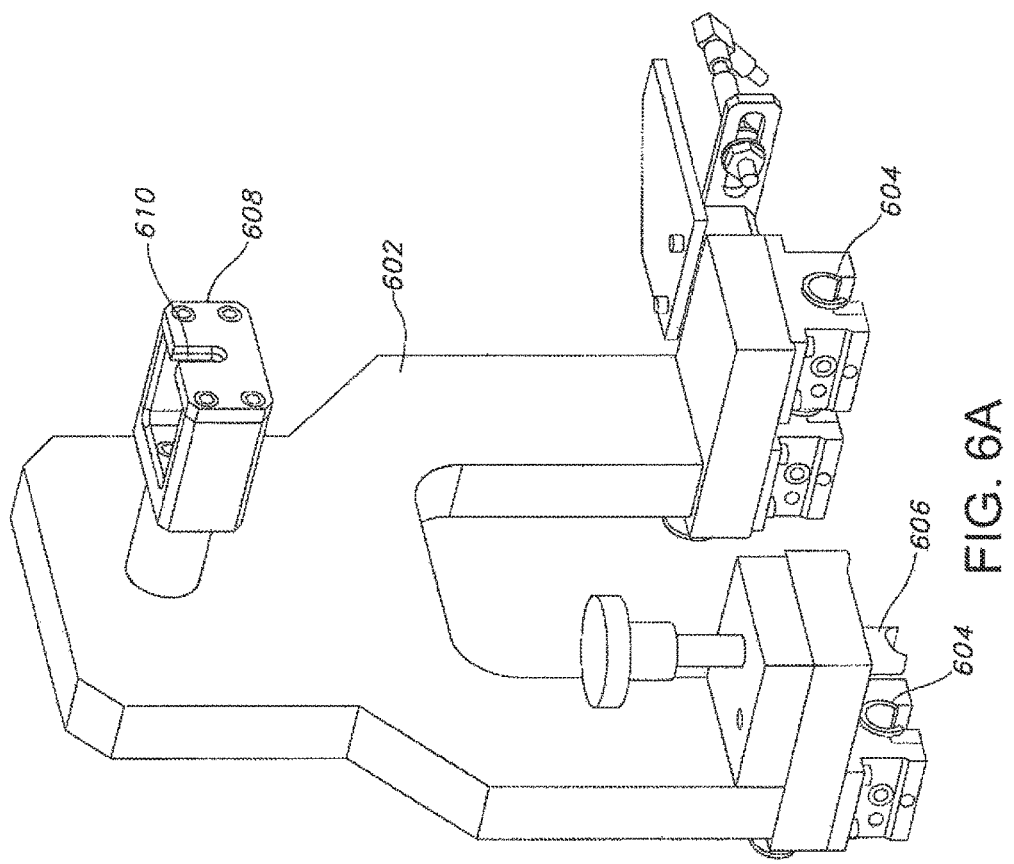

CHECKER BALLOON WINDING MACHINE

FIELD OF THE INVENTION

Generally, the present invention relates to balloon catheters including at least a catheter tube and an inflatable balloon. Particularly, it relates to methods and devices for providing a catheter tube having a concentrically disposed inflatable balloon, stent, stent graft, or combination thereof, wherein there is provided on the surface of the concentrically disposed inflatable balloon, stent, stent graft, graft, or combination thereof a predetermined pattern of surface indentations.

BACKGROUND OF THE INVENTION

It is well known in the medical arts to provide structures such as inflatable balloons, stents, stent grafts, grafts, and the like disposed concentrically on a distal end of a catheter. Such structures serve a variety of useful purposes, such as widening a vessel having an interior lumen (for example, a blood vessel) into which the catheter is inserted, forcing open a blocked or partially blocked vessel, delivering a stent, graft, or stent graft to a desired section of a vessel for unblocking or repair purposes, and the like. The dimensions and properties of such structures (length, thickness, flexibility and the like), and the materials from which they are fabricated, vary widely in accordance with the intended use thereof.

Using the balloon catheter as an example, it is desirable for the balloon, when in the deflated state, to define a low profile configuration, conforming to the exterior dimensions of the catheter distal end, for lesion crossability, trackability, and overall deliverability of the catheter. That is, it is desirable for the balloon, which is folded on and concentrically disposed around an exterior surface of the catheter, to increase the cross-sectional dimension of the catheter/balloon assembly as little as possible when deflated. This preserves the flexibility of the catheter and improves catheter tracking and deliverability of the catheter, particularly at the distal end on which the balloon is disposed, and reduces the potential for damage to the vessel wall during insertion/retraction of the catheter. Similarly, this minimizes introducer sheath compatibility.

To achieve this and other goals, it is known to define a pattern of indentations such as grooves, channels, relief structures, and the like (termed "checkering") on an exterior of a structure wrapped concentrically about a catheter, such as for example a deflated balloon, a stent, a graft, a stent graft, or the like. Upon inflating the balloon, such as with sterile saline or the like passed through the catheter lumen and therefrom into an interior of the balloon, the indentations substantially disappear as the balloon inflates. Upon deflating the balloon, the indentations reform, and may assist the balloon in reverting to the former, low profile configuration about the catheter. This reversion to the low profile configuration may assist in refolding of the device for reinsertion.

Such indentations may be molded, cut, or carved into the exterior surface of the balloon. However, this method increases labor and manufacturing costs. More desirably, the surface pattern of indentations may be defined in or on that exterior structure by winding a suitable material, such as a tape, beading, wire, fiber, filament, or the like around an exterior surface of the balloon, and applying heat and pressure to create the desired pattern of indentations. Prior winding methods for providing such a pattern of indentations, primarily involving manual winding, do not satisfactorily address quality control issues. Particularly, such manual methods do not provide suitable consistency in terms of tension applied to the filament, and also do not provide consistent catheter-to-catheter results in terms of the pitch of the wound line and the resulting pattern. Still further, heat and pressure-applying devices known in the prior art for catheter manufacture require constant re-adjusting/re-tooling to accommodate catheters of different lengths.

The present disclosure addresses a need in the art for methods and devices for providing such a pattern of surface indentations in an exterior surface of a balloon, stent, graft, stent graft, or combination thereof disposed concentrically about the distal tip of a catheter. In particular, improved methods and devices for automating the process of providing such surface indentations are disclosed. Even more, the present disclosure provides methods and devices for not only automating the process, but also for accommodating catheters of substantially any length without need for reconfiguration of the device. The presently disclosed invention meets this need in the art, while also contemplating good engineering practices, including relative inexpensiveness, stability, ease of implementation, low complexity, etc.

SUMMARY OF THE INVENTION

The above-mentioned and other problems become solved by applying the principles and teachings associated with the hereinafter-described methods and systems for providing surface indentations in an exterior surface of a balloon or other structure concentrically disposed on a distal end of a catheter. Broadly, the invention provides a device for providing such surface indentations using a tape, beading, wire, fiber, filament, or the like, wherein the surface indentations are provided by wrapping the tape, beading, wire, fiber, filament, or the like around an exterior of the balloon or other structure, and concurrently applying heat and pressure. Advantageously, the presently disclosed invention allows providing such surface indentations on an exterior surface of the balloon or other structure in a single pass.

Generally, in one aspect of the invention there is described a device for winding a filament around an exterior surface of a balloon catheter to provide a predetermined pattern of surface indentations in an exterior surface of the balloon. The device includes at least a controller, a rotatable holder for holding at least a distal end of a balloon catheter at opposed ends of a balloon disposed on the catheter distal end, and a translatable winding carriage for winding a filament around an exterior surface of the balloon disposed on the catheter distal end. The controller causes the translatable winding carriage to move along a longitudinal dimension of the balloon catheter to wind the filament around the balloon catheter at a predetermined pitch.

Typically, the translatable winding carriage includes at least a filament spool for holding a length of filament for winding around the balloon, a tensioner for applying a predetermined tensioning force to the filament during a filament winding step, and a heater such as a forced air heater for applying a predetermined amount of heat to a section of the balloon having a length of filament wound therearound. Thus, the filament is wound helically around the balloon catheter exterior, the balloon is heat set, and the predetermined pattern of surface indentations are provided in the balloon exterior surface in a single pass. The heating step occurs very shortly after the winding step, which reduces the risk of shifting of the wound line and disruption of the desired pattern and/or pitch.

A rotatable catheter body holder may also be provided for holding a portion of a catheter body not held by the catheter distal end holder. It will be appreciated that this feature provides a "one size fits all" advantage, in that a balloon catheter of any length may be accommodated for checkering without any need to reconfigure the device.

In another aspect, there is provided herein a method for winding a filament around an exterior surface of a balloon catheter to provide a predetermined pattern of surface indentations in an exterior surface of the balloon. Broadly, the method includes the steps of providing a holder for holding at least a distal end of a balloon catheter at opposed ends of a balloon disposed on the catheter distal end, rotating the balloon catheter held in the holder at a predetermined rate of rotation, and concurrently winding a filament under a predetermined amount of tensioning force helically along a longitudinal dimension of an exterior surface of the balloon catheter and applying a predetermined amount of heat from a heater to the filament wound helically around the balloon catheter to provide the predetermined pattern of surface indentations in the exterior surface of the balloon.

According to the present method, the filament and the heater concurrently travel along the longitudinal dimension of the balloon catheter to provide the predetermined pattern of surface indentations in the exterior surface of the balloon at a predetermined pitch in a single pass. Typically, the amount of tension applied to the filament, the amount of heat applied by the heater, and the rate of rotation of the balloon catheter are selected according to the physical dimensions and materials of fabrication of the balloon catheter to provide the predetermined pattern of surface indentations at the predetermined pitch.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIGS. 6a-b show a mandrel support and mandrel for use with the device of FIG. 1;

DETAILED DESCRIPTION OF THE ILLUSTRATED EMBODIMENTS

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention and like numerals represent like details in the various figures. Also, it is to be understood that other embodiments may be utilized and that process, mechanical, electrical, arrangement, software and/or other changes may be made without departing from the scope of the present invention. In accordance with the present invention, devices and methods for providing a predetermined pattern of surface indentations in an exterior surface of a balloon of a balloon catheter are hereinafter described.

The following discussion describes an embodiment of the present invention, wherein a pattern of surface indentations is provided on an exterior surface of a balloon disposed concentrically around an exterior of a catheter distal end, which process is known as "checkering" in the art. The skilled artisan will appreciate that the description applies likewise to a balloon, a stent, a stent graft, or any desired combination thereof disposed concentrically around an exterior of the catheter distal end, without consideration of undue experimentation. Further, the described embodiment utilizes a nylon filament for imposing the surface indentations, but the skilled artisan will similarly realize that any alternative structure of any suitable material according to the size and shape of the desired surface indentations may be utilized, including without limitation a tape, beading, wire, fiber, filament, or the like without undue experimentation.

Figure 1:
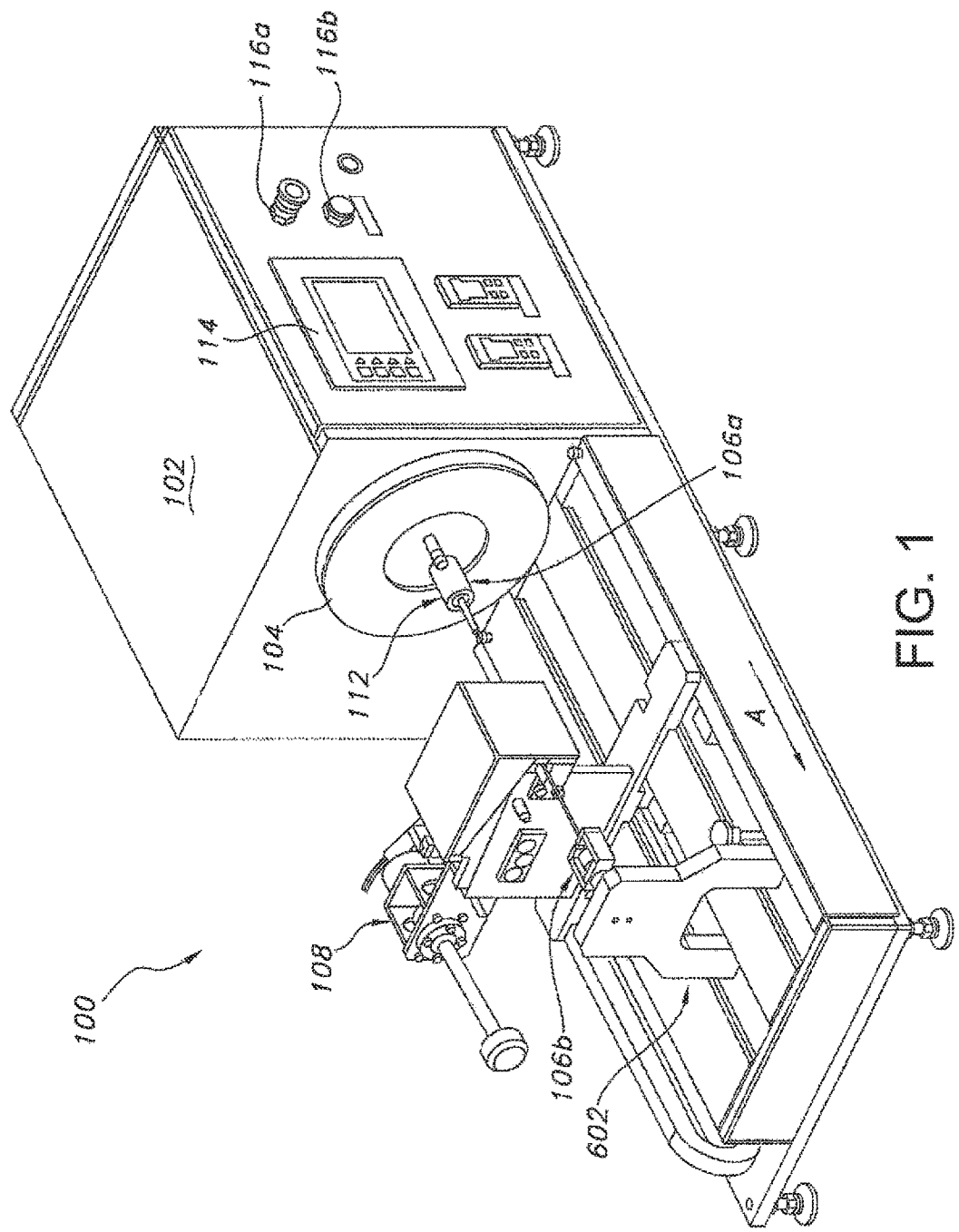
FIG. 1 shows a front view of a device for imposing a pattern of surface indentations on a balloon catheter.

With reference to FIG. 1, a representative device 100 for providing a pattern of surface indentations on an exterior surface of a balloon, stent, stent graft, or combination thereof disposed concentrically around an exterior of a catheter distal end is shown. The device 100 includes at least a controller 102, a catheter body holder 104, catheter distal end holders 106a,b for holding a catheter distal tip (not shown in this view) at opposed ends, and a translatable winding carriage 108.

Figure 2:
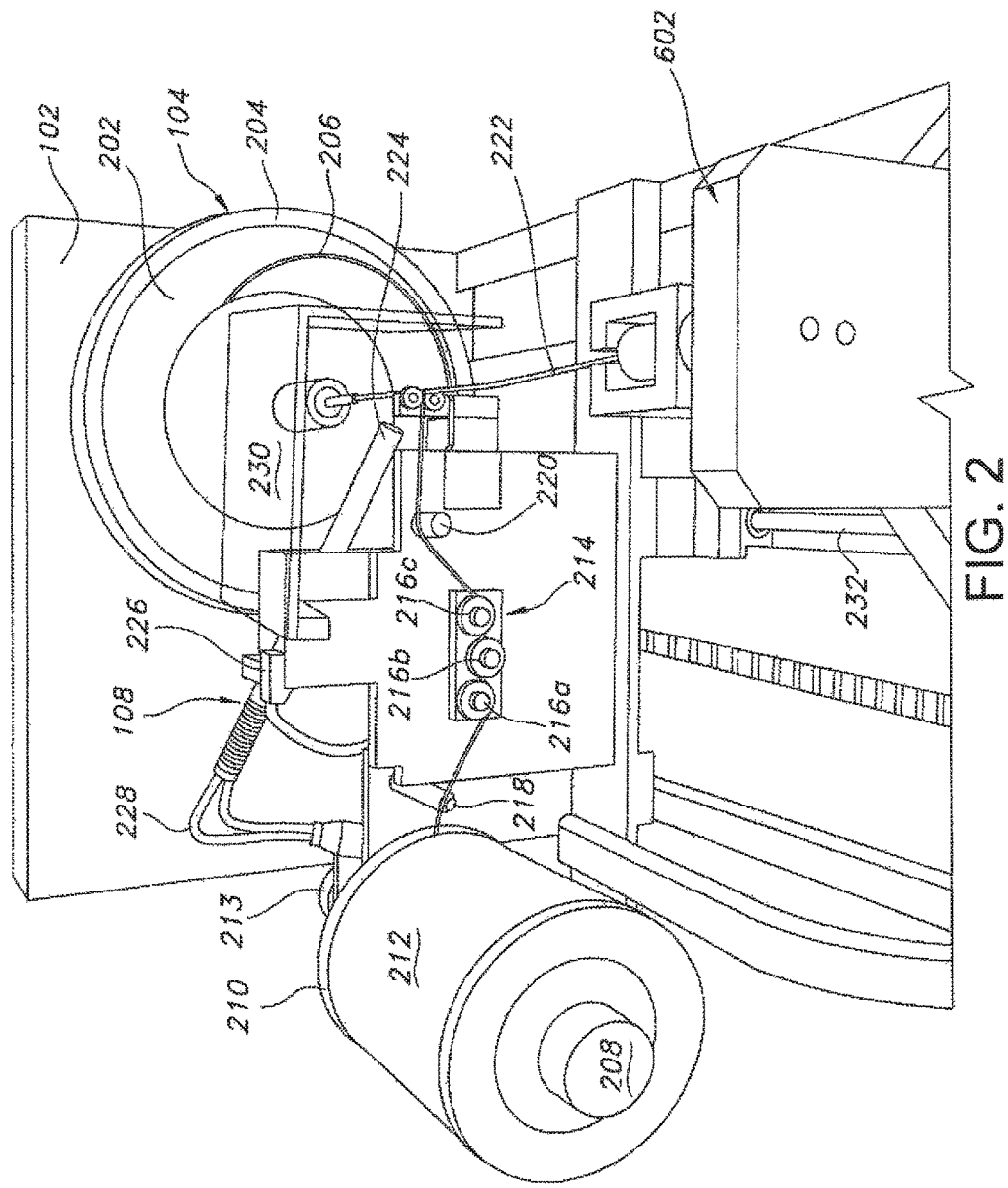
FIG. 2 is a side view of the device shown in FIG. 1.

With reference to FIG. 2, the catheter body holder 104 in the embodiment shown includes a circular body 202 and a raised circumferential lip 204 for retaining the catheter body in place. It will be appreciated that the user need only place the catheter body (shaft) 206 in an interior of the catheter body holder 104, thereby conveniently storing the catheter body 206 during a winding operation described in detail below. Thus, regardless of the length of the catheter to be checkered, the present device 100 can accommodate it without reconfiguration of any part thereof.

FIG. 2 also shows the winding carriage 108, which in the depicted embodiment includes a spool holder 208 and a spool 210 for holding the structure used to provide the surface indentations, in the depicted embodiment being a reel of nylon filament 212. The nylon filament is passed through a sensor 214, in the depicted embodiment being arrayed pulleys 216 a,b,c, which operate substantially as a tensiometer for measuring a tension applied to the nylon filament 212. The specific tensioning force applied to the filament 212 is determined by an electromagnetic braking system 213, which serves as a continuously variable clutch under the control of the controller 102 as will be described below. In the depicted embodiment, electromagnetic braking system 213 acts as a continuously variable clutch which applies more or less resistance to rotation in accordance with the amount of current applied. The tensiometer (pulleys 216 a,b,c) measures the tension applied to filament 212 created by that resistance to rotation, and provides feedback to the controller 102 to maintain that tension at a constant, predetermined value. It is contemplated to apply tension to the filament 212 of from about 100 g to about 500 g to provide the desired checkering pattern.

Additional guiding posts 218, 220, which may also include pulleys, are included to support the filament 212. From guide post 220, the filament 212 is passed to a supporting follower (see below) disposed near a balloon catheter 222 held in the catheter distal end holders 106a,b.

The winding carriage 108 also supports a heater 224, in the depicted embodiment being a forced air heater of substantially conventional design for applying a predetermined amount of heat to a balloon catheter held in the catheter distal end holders 106a,b. The depicted embodiment includes a heat element 226 for providing heat in any desired range, and an air source/tubing 228 for passing air through the heater 224 at a desired rate to contact a balloon catheter 222 held in holder 106. It will be appreciated that additional structures (not shown) associated with the heater 224 are contemplated, such as nozzle extensions/tips for further focusing airflow and heat to a desired point on the catheter 222. It is contemplated to provide a heat element 226 providing heated air in a heating range of from about 45° C. to about 120° C., and an air source/tubing 228 providing an air flow at from about 30 to about 50 liters/minute. The specific heat and air flow applied to the filament 212 are determined by the controller 102 as will be described below. A safety shield 230 may also be provided for user safety.

The heater 224 is configured to apply precise heating to a balloon catheter at a predetermined distance behind the point at which the filament 212 is wrapped around the balloon catheter, to create (in combination with a tension applied to the filament, discussed in greater detail below) the desired pattern of surface indentations in the balloon exterior surface. In the depicted embodiment, the heater is held on the winding carriage 108 whereby heat is applied to a position about one inch behind the point at which the filament 212 is wrapped around the balloon catheter. Of course, it will be appreciated that this distance may vary in accordance with any number of parameters.

Figure 3:
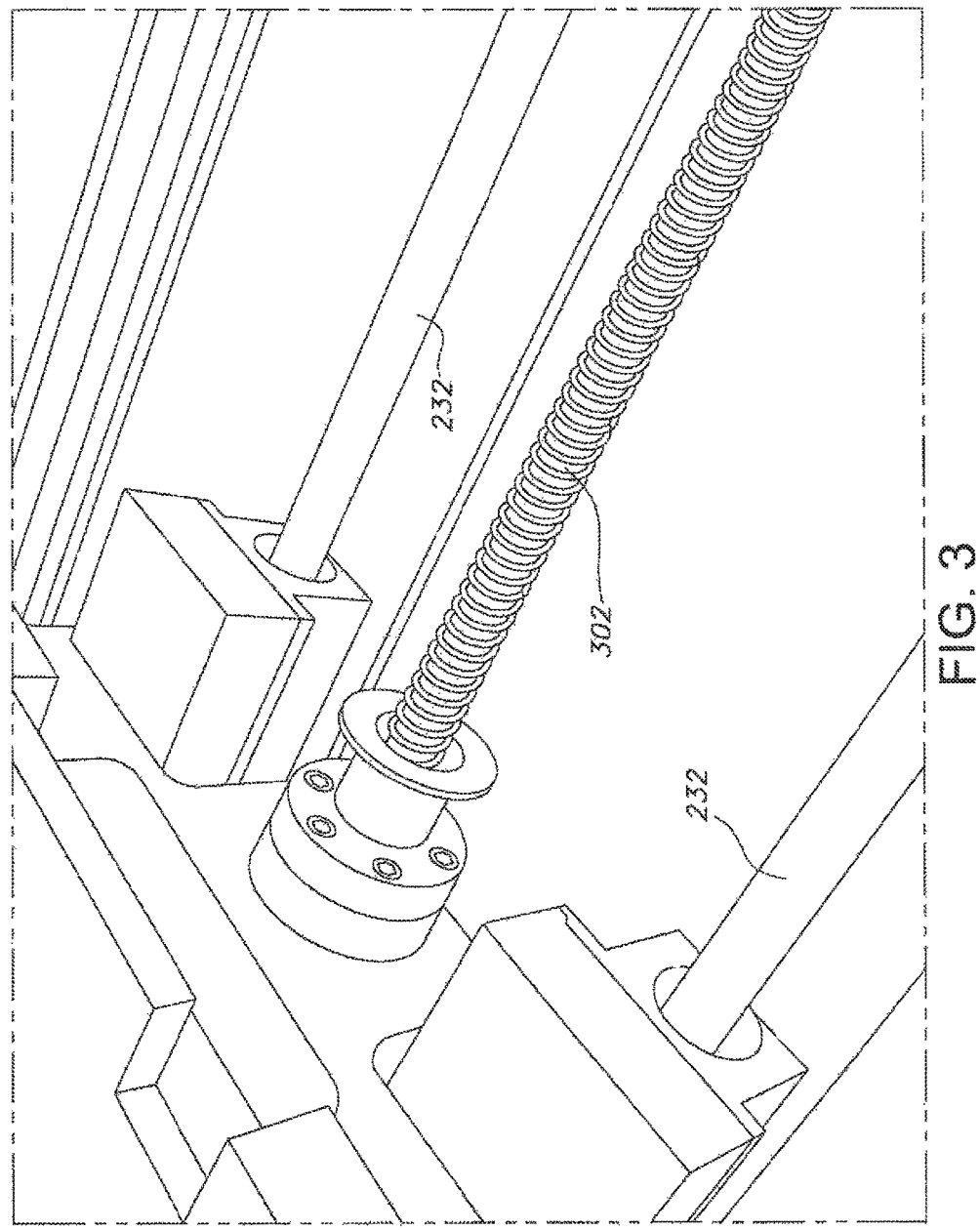
FIG. 3 shows a screw drive for use with the device of FIG. 1.
Figure 4:
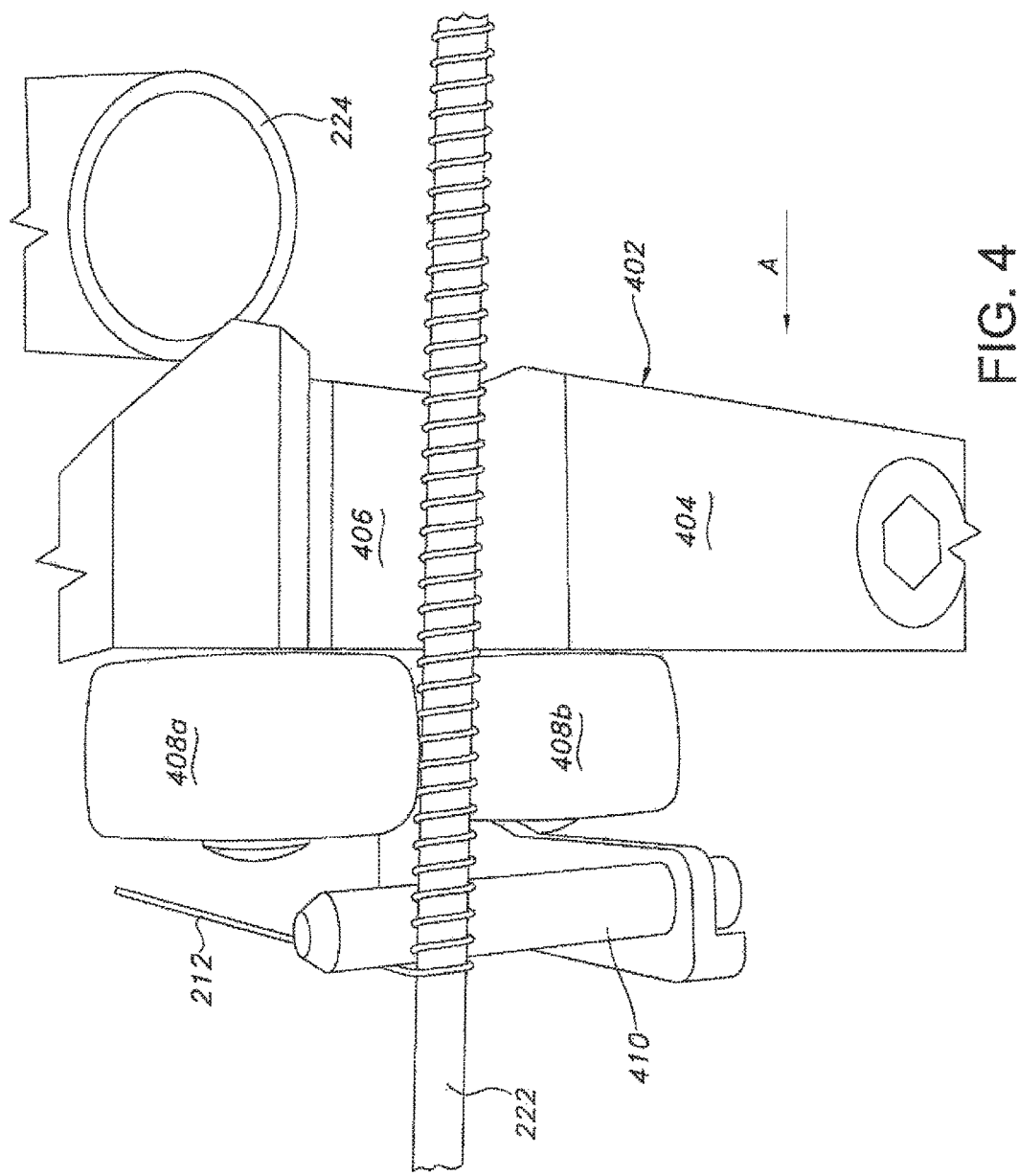
FIG. 4 shows a supporting follower for use with the device of FIG. 1.

The winding carriage 108 is configured to be translatable laterally along one or more tracks or shafts 232, in a direction parallel to a balloon catheter 222 held in the catheter distal end holders 106a,b (see arrow A in FIGS. 1 and 4). This may be accomplished by any suitable method, in the embodiment shown in the Figures being a screw drive 302 (see FIG. 3). The rate at which the winding carriage 108 is translated is determined by the controller 102 and provided to the motor.

FIG. 4 shows a supporting follower 402 for use in wrapping the filament 212 around a balloon catheter 222. Generally, the supporting follower 402 includes a support bar 404 having a notch or groove 406 for receiving the catheter 222. Paired rollers 408a,b rotatably support the catheter 222, allowing the catheter 222 to rotate freely therebetween. A guide pin 410 both supports catheter 222 and guides filament 212 as the filament 212 wraps around the catheter 222 in the manner which will be described in detail below. In use, the winding carriage 108 travels in the direction denoted by arrow A. As the catheter 222 rotates, the filament 212 winds thereabout. The skilled artisan will appreciate that in accordance with the diameter of the balloon catheter to be checkered and the parameters input into the device 100, any suitable pitch may be provided. A pitch of from about 0.5 mm to about 3 mm is contemplated, with the wound filament defining an included angle of from about 0 to about 45° from the vertical. Of course, this will be determined by a variety of factors, including the rate of travel of the winding carriage 108, the rate at which the balloon catheter 222 is rotated, etc. In the depicted embodiment, a helical pattern is provided having a pitch of about 1 mm. The edge-to-edge spacing (between adjoining filament 212 loops) in this view is on the order of about 1 mm.

Figure 5:
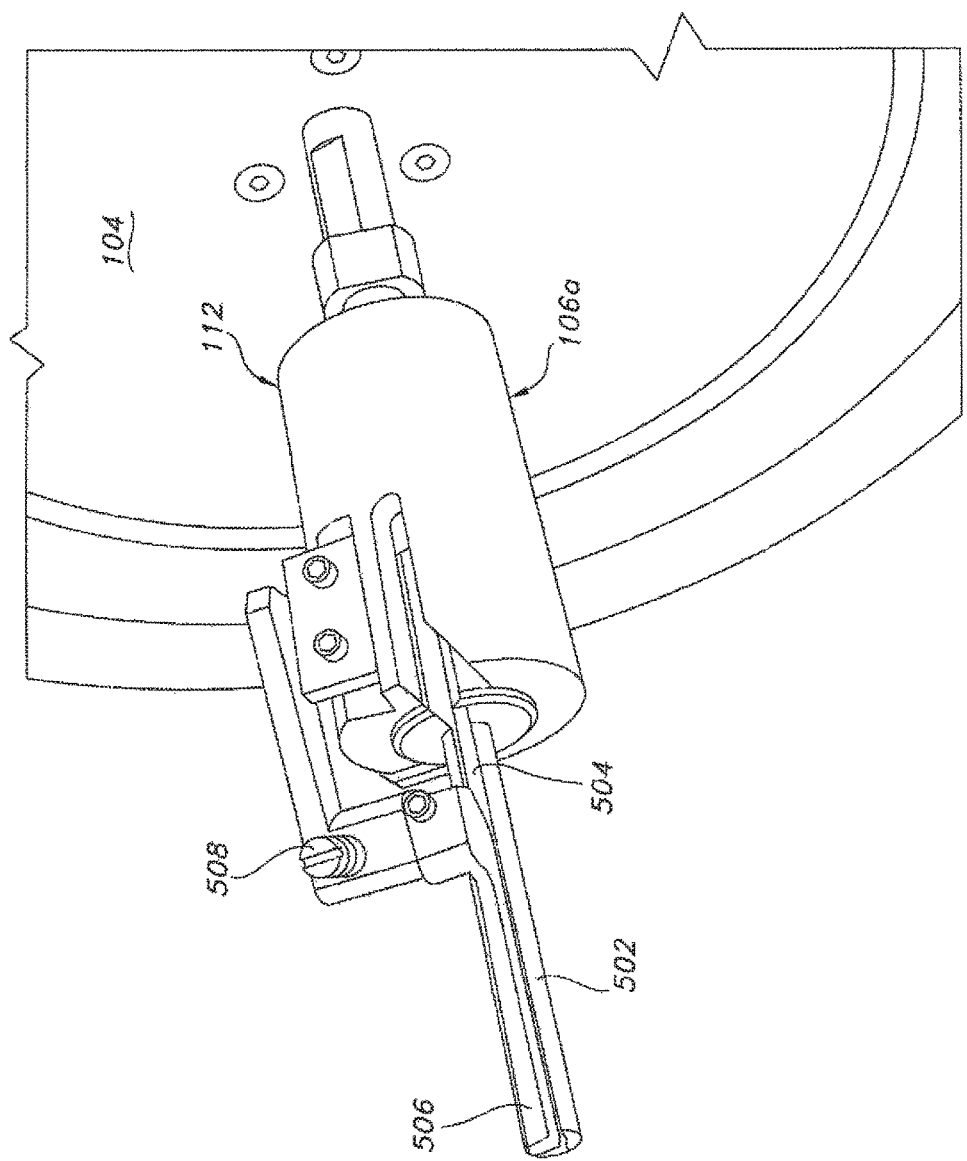
FIG. 5 shows a rotatable clamp for use with the device of FIG. 1.

Catheter distal end holder 106a includes a clamping assembly 112 (see FIG. 5). Clamping assembly 112 includes a central guide post 502 having a groove 504 for receiving a catheter body proximal to the balloon to be wound (not shown). A spring-loaded clamp 506 is included, for holding a catheter body in place. Spring-loaded clamp 506 also includes a tie post 508 to which the filament 212 may be secured during operation of the device. The clamping assembly 112 further includes a detent (not shown for convenience) for retaining the spring-loaded clamp 506 in the open position, such as when a catheter is to be loaded or unloaded. Clamping assembly 112 is rotatably attached to catheter body holder 104, such that the clamping assembly 112 rotates when the holder 104 rotates.

FIG. 6a shows a mandrel support assembly 602, including channels 604 adapted for receiving and sliding along tracks or shafts 232. A friction brake 606 reversibly secures mandrel support assembly 602 in place at the desired position on tracks or shafts 232. Mandrel support assembly 602 further includes a mandrel support 608 defining a receiver, and having a slot 610 in a wall thereof.

Figure 6B:
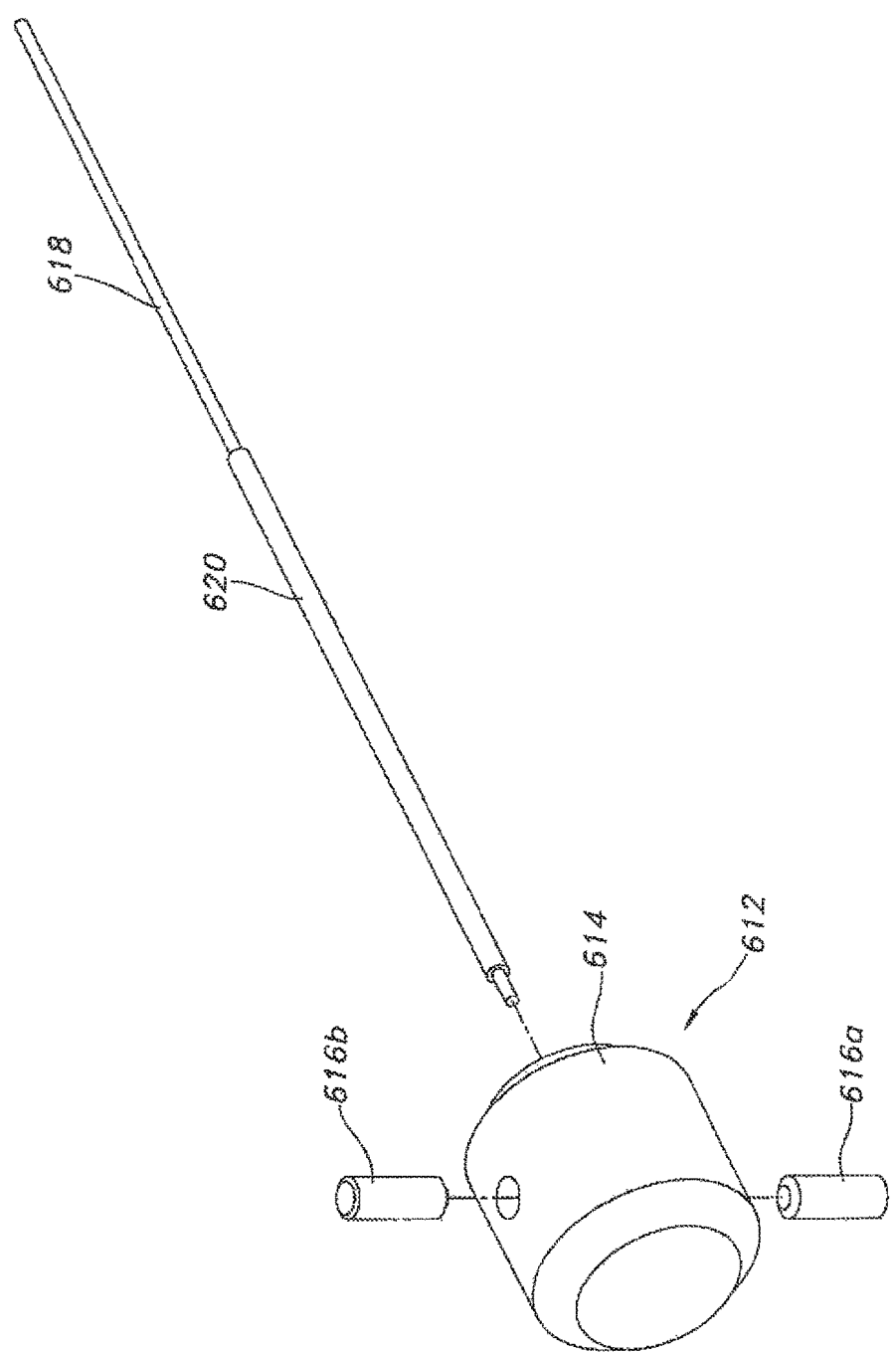

FIG. 6b shows a mandrel assembly 612 for receiving a catheter 222 distal tip (not shown in this view). The mandrel assembly 612 includes a mandrel adapter 614 having an aperture (not shown in this view) for receiving a mandrel 618 and guard 620 therein. Set screws 616a,b or other suitable fasteners retain the mandrel end in place, preventing inadvertent removal from the mandrel adapter 614. The distal tip guard 620 may be provided to protect the catheter 222 distal tip (not shown) from damage.

In use, a portion of mandrel 618 is sleeved by the lumen of a catheter 222 distal tip (not shown). A portion of the catheter 222 distal tip is in turn sleeved in a lumen of distal tip guard 620 such that the distal tip is protected from damage. This assembly is inserted in the aperture in mandrel adapter 614, and secured in place with set screws 616a,b. Next, mandrel adapter 614 with distal tip guard 620/mandrel 618 received therein is placed in the receiver defined by mandrel support 608. Distal tip guard 620 rotatably rests in slot 610. The position of mandrel support assembly 602 is adjusted as necessary along tracks or shafts 232, in accordance with the length of catheter 222 (held by catheter distal end holders 106a,b) to be checkered. The catheter 222 is then ready for the checkering operation as described above.

It will be noted that mandrel adapter 614 may rotate freely in mandrel support 608, whereby when a catheter 222 is secured in catheter distal end holders 106a,b and catheter body holder 104 rotates, both mandrel adapter 614 and clamping assembly 112 rotate at the same rate to ensure consistent rate of rotation for each of the opposed ends of a balloon catheter 222 held therein. Alternatively, both mandrel adapter 614 and clamping assembly 112 may rotate under the control of one or separate motors (not shown).

The controller 102 may be configured for data entry by any of a number of substantially conventional methods, such as a user input panel 114 which may include pressure switches or a touch screen (see FIG. 1) and the like. In this manner, in accordance with the physical dimensions of a particular balloon catheter, the materials from which the catheter is fabricated, and the like, the user may input the desired parameters defining a specific winding speed, tension applied to filament 212, and air heat emanating from heater 224. Alternative data input methods are also contemplated. For example, it is known to incorporate information relating to the above parameters, that is, physical dimensions of a particular balloon catheter, the materials from which the catheter is fabricated, and the like, predetermined winding speed, tension applied to filament 212, and air heat, in scannable means such as a bar code. Accordingly, it is contemplated also to provide a scanner such as a bar code scanner (not shown in this embodiment) for retrieving data relating to the particular balloon catheter design on which surface indentations are to be imposed according to the present invention.

Figure 7A:
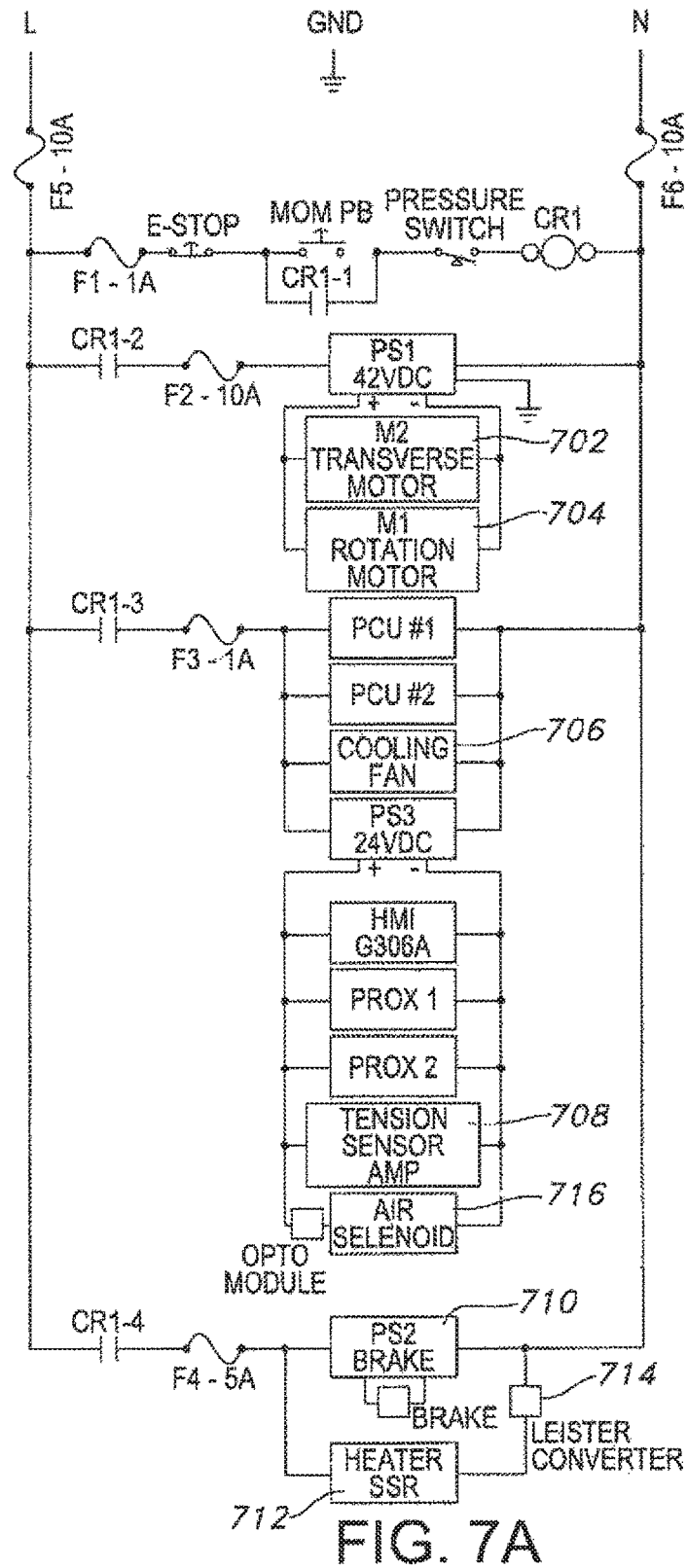
FIGS. 7a-c show components of the device of FIG. 1 in schematic form.
Figure 7B:
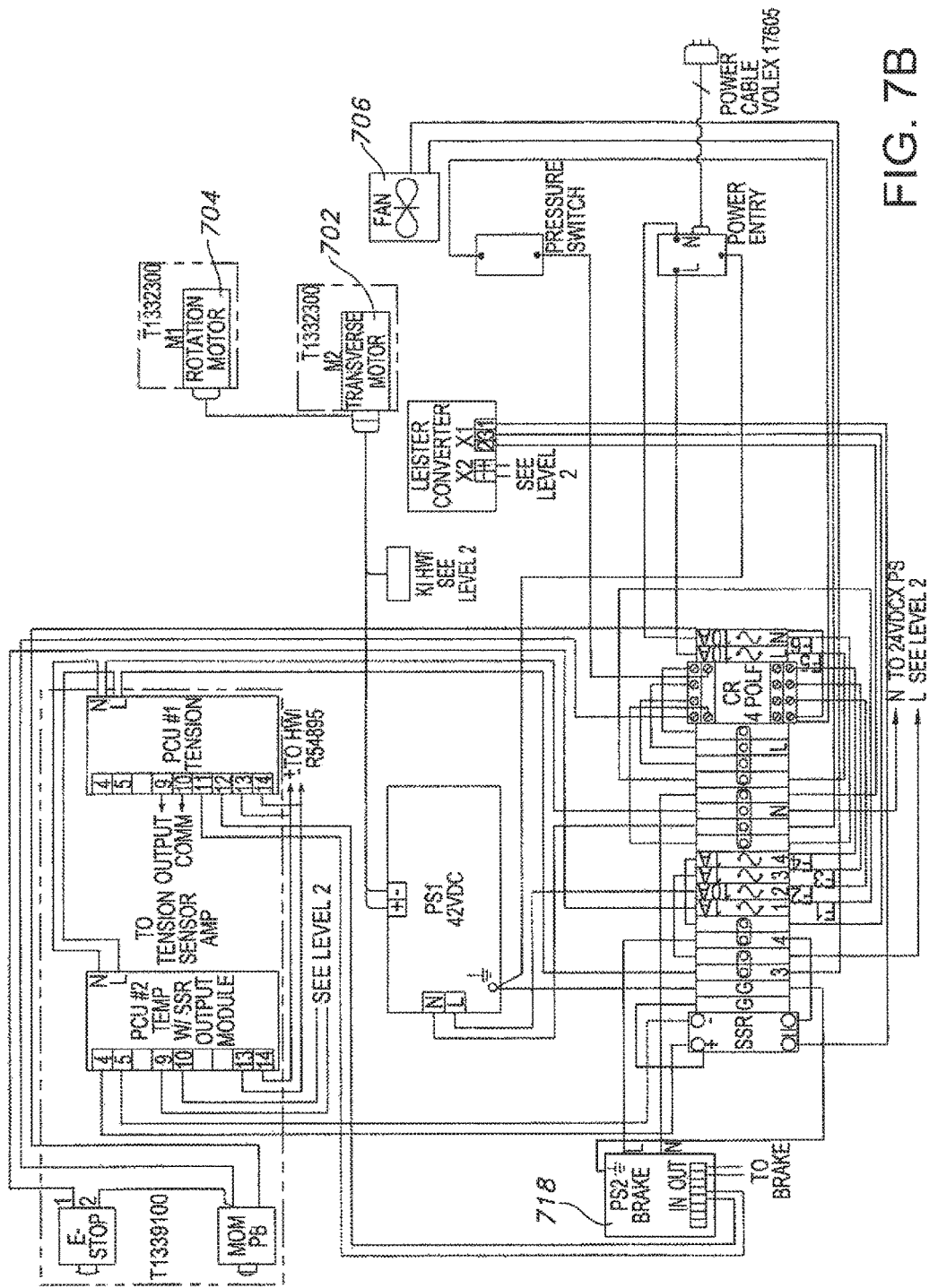
Figure 7C:
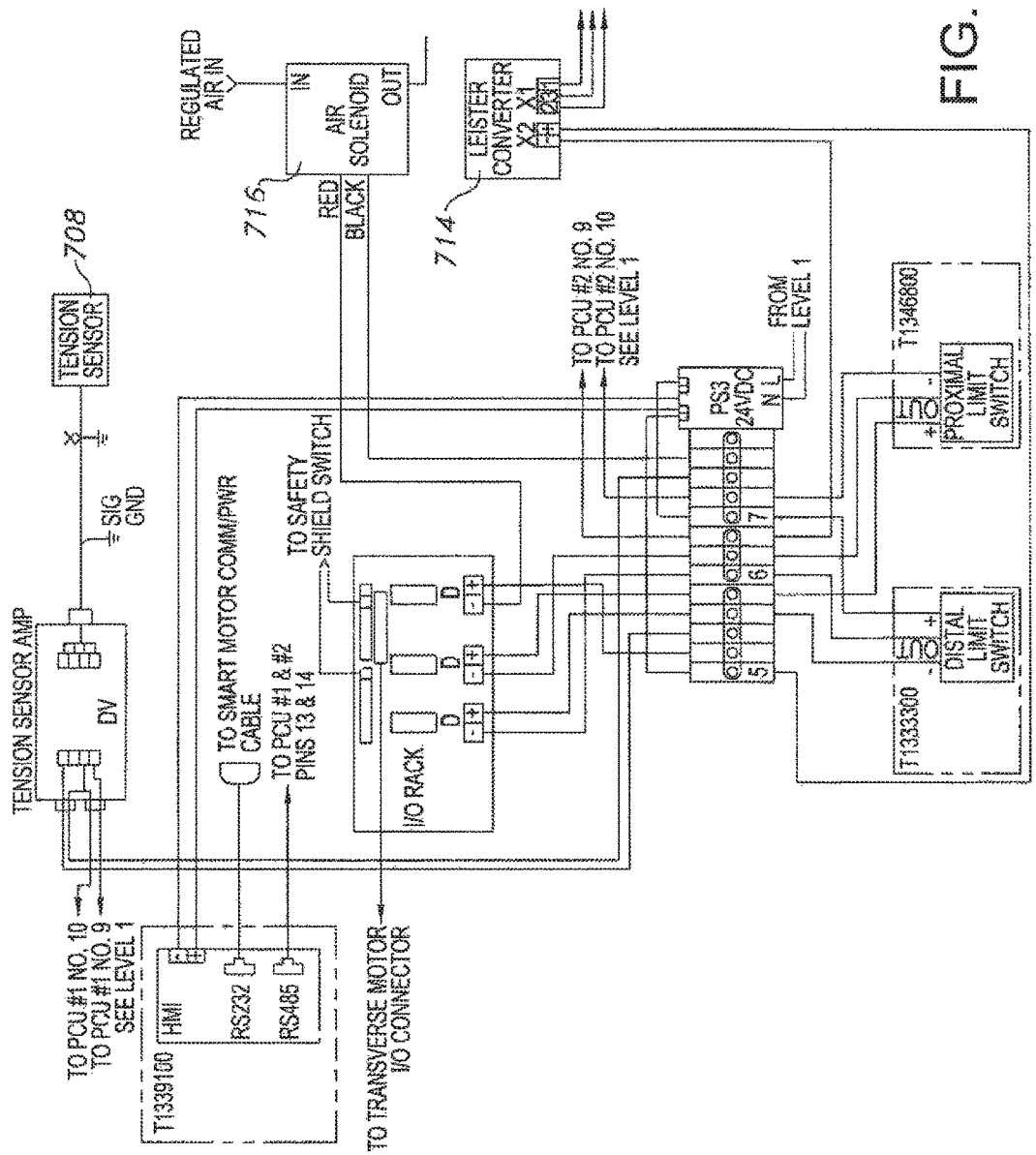

Various components controlling the device 100 are represented schematically in FIGS. 7a-c. First and second motors 702, 704 are provided, for controlling transverse motion of winding carriage 108 and rotation of catheter body holder 104, respectively. A cooling fan 706 is provided for cooling an interior of controller 102. A tension sensor 708 provides feedback to controller 102, ensuring regulation of the amount of tension applied to filament 212. A brake 710, in the depicted embodiment being an electromagnetic braking system, controls the amount of torque required to rotate spool 210. Likewise, a rotation motor 704 controls rotation of the catheter body holder 104. Control of heater 224 is controlled by a solid state relay 712. A converter allows precise control of the temperature of air flowing from air source 228. Initiation and termination of airflow may be regulated by a solenoid 716. Inputs 116 represent switches, such as an emergency stop switch 116a for a user to stop all movement in an emergency situation, and a momentary switch 116b to supply power to start the device 100. Additional circuit wiring and components are depicted also.

In use (see FIG. 2), a balloon catheter 222 is loaded into catheter distal end holders 106a,b, and secured at each end of the balloon by mandrel support assembly 602/mandrel assembly 612 and clamping assembly 112. It will be appreciated that the balloon catheter 222 may also include additional components concentrically disposed on or under the balloon, such as stents, grafts, stent grafts, etc. (not shown). The remainder of the catheter 222 body is held in catheter body holder 104, preventing interference by the catheter body. Filament 212 is passed through tensiometer pulleys 216a-c, and over guide posts 218 and 220, and secured to tie post 508.

According to the specific dimensions, materials, and the like of a specific balloon catheter/stent/stent graft (i.e., diameter and length of balloon, materials from which the balloon is fabricated, etc.), the user inputs specific parameters of air temperature from heater 224, rate of travel of winding carriage 108, and tension applied to filament 212 in order to achieve a specific pitch (i.e., the number of times filament 212 is wound around balloon catheter 222 over a predetermined distance). Air flow rate may be fixed (in one non-limiting embodiment being 35 L/min.), or may be variable from about 30 to about 50 L/min. to accommodate multiple materials for fabricating balloons for catheters as are known in the art.

Without intending any limitation, in one specific embodiment as applied to a balloon catheter of substantially conventional dimensions and materials, a tension of about 240 grams is applied to a nylon filament 212 (20 pound test) and a winding carriage 108 rate of travel of from about 2 to about 5 cm/min. is established with application of heat as described above, providing an edge to edge gap (between adjoining loops of filament 212) or pitch of about 1 mm to provide the desired surface pattern of indentations.

As discussed above, this may be accomplished by any number of ways, such as by manually inputting the data. Alternatively, controller 102 may be provided with a CPU and memory storage capacity allowing storage of particular operating conditions associated with a specific catheter type, for example coded to a product trade name. In this scenario, the user need only input the product name or other selected coding parameter, and the controller 102 will input the necessary operating parameters to provide the desired pitch. Still further, as noted above it is contemplated to provide the necessary physical dimensions of the balloon catheter (or alternatively the coding allowing controller 102 to select the predetermined operating parameters for the particular catheter to be checkered) using scannable means such as a bar code.

Figure 8:
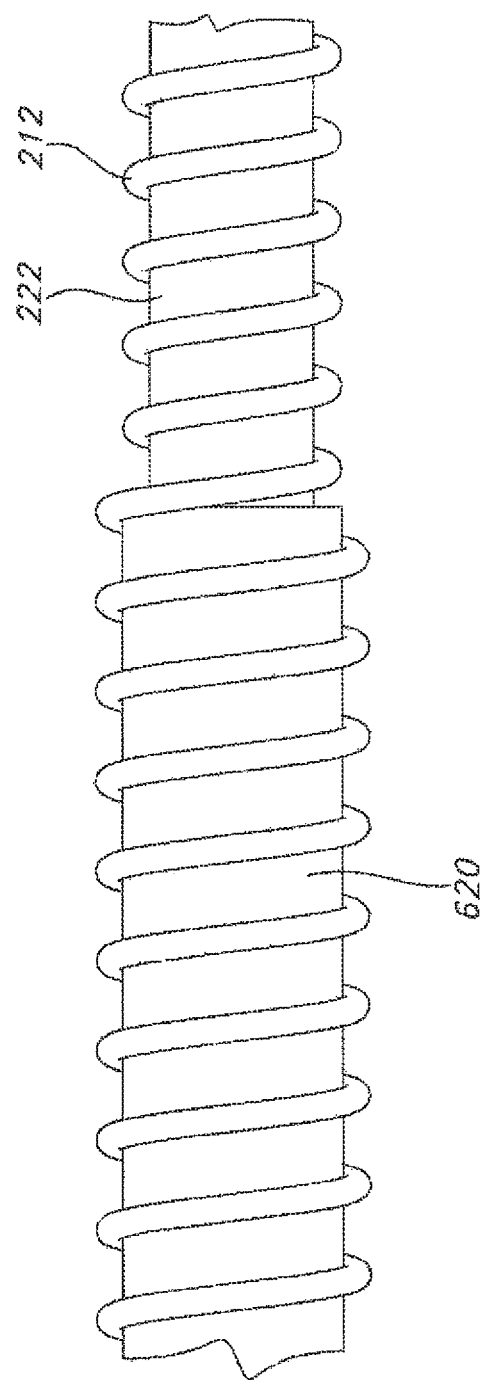
FIG. 8 shows a filament wrapped around a balloon catheter and protector by the method and device described herein.

After inputting the desired parameters, catheter body holder 104 rotates (and concurrently catheter distal end holders 106a,b and catheter 222 rotate at the same rate) at the predetermined rate of rotation necessary to achieve the desired pitch. Concurrently, winding carriage 108 traverses laterally (parallel to a longitudinal dimension of catheter 222, see arrow A in FIGS. 1 and 3), winding filament 212 helically around the longitudinal dimension of balloon catheter 222 at a predetermined pitch (see FIG. 8). Also concurrently, heater 224 is activated and applies a predetermined heat and airflow to a section of balloon catheter 222 (with filament 212 wound thereon), softening the material of balloon catheter 222 and heat-setting the balloon folds. Because filament 212 is under a predetermined tension, a surface indentation is created in the exterior surface of the balloon. This process continues along the predetermined length of the balloon portion of balloon catheter 222. Filament 212 is wound a short distance over distal tip guard 620 (see FIG. 8) to ensure that the entire surface of the balloon receives the desired pattern of surface indentations. At this stage the controller 102 may terminate the process. The user then need only cut filament 212, remove balloon catheter 222 from the device 100, and remove filament 212 from the surface of balloon catheter 222, leaving the desired pattern of surface indentations. The device 100 may then reset, manually or automatically, and is ready for the next balloon catheter.

The depicted embodiment of the invention shows a device and method for providing a pattern of surface indentations in an exterior surface of a balloon catheter. However, as noted above, it is known also to concentrically overlap other structures over a balloon of a balloon catheter 222, such as without limitation stents, stent grafts, and the like. The skilled artisan will readily appreciate that the present device and method are easily adaptable to these alternative structures, such as by inputting data informative of any additional dimensions of thickness or length added by the additional structures, in the manner described for the balloon. Thus, it is readily apparent that the present device and method also serve to provide desired patterns of surface indentations in an exterior surface of such stents, stent grafts, etc. concentrically disposed on a balloon catheter, to confer the same desired properties of a low profile configuration conforming to the exterior dimensions of the catheter distal end, improved catheter flexibility, and improved reformation and reversion of the balloon to the low profile configuration upon deflation.

Certain advantages of the invention over the prior art should now be readily apparent. The skilled artisan will readily appreciate that by the present disclosure is provided a simple, efficient, and economical process, and an automated device for accomplishing the process, for providing a desired pattern of surface indentations in an exterior surface of a balloon catheter. The device accommodates any length of catheter via the catheter body holder. In particular, the present process and device allow automated surface indentation of a balloon catheter of any length in a single pass, reducing the amount of labor required. That is, the steps of winding a filament, tape, bead, or the like under tension around a balloon catheter and applying heat to create the desired surface pattern are accomplished automatically and in substantially a single step, reducing manufacturing time and costs. Even more, the automated nature of the process provides a way to achieve a repeatable, precisely controlled pattern of surface indentations in a balloon catheter, markedly improving quality control parameters from balloon catheter to catheter.

Finally, one of ordinary skill in the art will recognize that additional embodiments are also possible without departing from the teachings of the present invention. This detailed description, and particularly the specific details of the exemplary embodiments disclosed herein, is given primarily for clarity of understanding, and no unnecessary limitations are to be implied, for modifications will become obvious to those skilled in the art upon reading this disclosure and may be made without departing from the spirit or scope of the invention. Relatively apparent modifications, of course, include combining the various features of one or more figures with the features of one or more of other figures.

The invention claimed is:

1. A method for providing surface indentations in an exterior surface of a balloon catheter, comprising:
   providing a holder for holding at least a distal end of the balloon catheter;
   rotating the balloon catheter while held in the holder; and
   winding a filament helically along the exterior surface of the balloon catheter.

2. The method of claim 1, wherein the winding step comprises winding the filament at a predetermined pitch in a single pass.

3. The method of claim 1, wherein the balloon catheter includes at least one structure including the exterior surface selected from the group comprising a balloon, a stent, a graft, and a stent graft, and the winding step comprises winding the filament along the exterior surface of the structure.

4. The method of claim 1, including applying a tensioning force to the filament of from about 100 g to about 500 g.

5. The method of claim 1, including winding the filament helically along the exterior surface of the balloon catheter at a pitch of from about 0.5 mm to about 3 mm between adjoining filament loops.

6. The method of claim 1, further including the step of applying heat from a heater to the filament.

7. The method of claim 6, further including applying heat to the balloon catheter and filament from about 45° C. to about 120° C.

8. The method of claim 6, wherein the filament and the heater are caused to concurrently travel along the balloon catheter at a rate of travel of from about 2 to about 5 cm/min.

9. The method of claim 1, further including the step of removing the filament wound around the longitudinal dimension of the exterior surface of the balloon catheter to expose the surface indentations.

10. The method of claim 1, wherein the winding step comprises winding the filament at an angle of about 45° from the vertical.

11. A method for preparing a balloon catheter for use, comprising:
    while rotating the balloon catheter, applying a filament along the exterior surface of the balloon catheter to form surface indentations therein.

12. The method of claim 11, further including the step of applying heat to the balloon catheter.

13. The method of claim 11, wherein the applying step comprises winding the filament at a predetermined pitch.

14. The method of claim 11, further including the step of removing the filament to expose the surface indentations.

15. The method of claim 11, wherein the applying step comprises winding the filament at an angle of about 0 to 45° from the vertical.

16. A method for providing surface indentations in an exterior surface of a balloon associated with a catheter, comprising:
    while rotating the catheter, winding a filament helically along the exterior surface of the balloon at a predetermined pitch;
    heating the balloon; and
    removing the filament to expose the surface indentations.

17. The method of claim 16, wherein the winding step comprises winding the filament at an angle of about 0 to 45° from the vertical.

* * * * *